US008735853B2

(12) United States Patent
Ayliffe

(10) Patent No.: US 8,735,853 B2
(45) Date of Patent: May 27, 2014

(54) FLUORESCENCE FLOW CYTOMETRY

(75) Inventor: Harold E. Ayliffe, Hailey, ID (US)

(73) Assignee: E.I. Spectra, LLC, Hailey, ID (US)

(*) Notice: Subject to any disclaimer, the term of this patent is extended or adjusted under 35 U.S.C. 154(b) by 3 days.

(21) Appl. No.: 13/492,805

(22) Filed: Jun. 9, 2012

(65) Prior Publication Data

US 2013/0327957 A1    Dec. 12, 2013

(51) Int. Cl.
*G01J 1/58* (2006.01)
*G01N 21/64* (2006.01)

(52) U.S. Cl.
CPC .......................... *G01N 21/64* (2013.01)
USPC .................................... 250/459.1; 250/458.1

(58) Field of Classification Search
CPC ........................................................ G01N 21/64
USPC ............................................ 250/459.1, 432 R
See application file for complete search history.

(56) References Cited

U.S. PATENT DOCUMENTS

| | | | | |
|---|---|---|---|---|
| 6,656,431 B2* | 12/2003 | Holl et al. | | 422/68.1 |
| 6,703,819 B2* | 3/2004 | Gascoyne et al. | | 324/71.4 |
| 8,502,148 B2* | 8/2013 | Wagner et al. | | 250/338.1 |
| 2002/0147317 A1* | 10/2002 | Bentsen et al. | | 536/8 |
| 2003/0036206 A1* | 2/2003 | Chien et al. | | 436/180 |
| 2007/0292941 A1* | 12/2007 | Handique et al. | | 435/288.7 |
| 2010/0288941 A1* | 11/2010 | Ayliffe et al. | | 250/432 R |
| 2012/0307244 A1* | 12/2012 | Sharpe et al. | | 356/338 |

* cited by examiner

*Primary Examiner* — David Porta
*Assistant Examiner* — Faye Boosalis
(74) *Attorney, Agent, or Firm* — Brian C. Trask

(57) ABSTRACT

A flow cytometer including a laser, indexing structure, adjustment structure, and sensor structure. The cytometer is conventionally used with a removable microfluidic cassette, which is installed at a first position that is enforced by the indexing structure. The adjustment structure changes a relative position between an interrogation aperture of the cassette and the laser beam. Feedback from the sensor structure is used to optimize propagation of the laser through the interrogation aperture to reduce (and hopefully eliminate) autofluorescence caused by beam impingement onto the cassette.

21 Claims, 11 Drawing Sheets

FLUORESCENCE FLOW CYTOMETRY

BACKGROUND OF THE INVENTION

1. Field

This invention relates to apparatus and methods for performing flow cytometry on particles that undergo a Stokes-shift emission of radiation. Preferred embodiments are structured to optimize a signal-to-noise ratio for such emission radiation.

2. State of the Art

Pioneering work in particle detection by measuring impedance deviation caused by particles flowing through a small aperture between two containers of electrically conductive fluid is disclosed in U.S. Pat. No. 2,656,508 to W. H, Coulter. Coulter's name is now associated with the principle of particles causing a change in electric impedance as they occlude a portion of the aperture. Since publication of his patent in 1953, considerable effort has been devoted to developing and refining sensing devices operating under the Coulter principle. Relevant US patents include U.S. Pat. No. 5,376,878 to Fisher, U.S. Pat. No. 6,703,819 to Gascoyne et al., U.S. Pat. No. 6,437,551 to Krulevitch et al., U.S. Pat. No. 6,426,615 to Mehta, U.S. Pat. No. 6,169,394 to Frazier et al., U.S. Pat. No. 6,454,945 and U.S. Pat. No. 6,488,896 to Weigl et al., U.S. Pat. No. 6,656,431 to Holl et al., and U.S. Pat. No. 6,794,877 to Blomberg et al. Patent application 2002/117,517 to Unger et al. is also relevant. Each above-referenced document is hereby incorporated by reference, as though set forth herein in their entireties, for their disclosures of relevant technology and structure employed in various sensor arrangements.

Flow cytometry is a well established technique that is used to determine certain physical and chemical properties of microscopic particles by sensing certain optical properties of the particles. Many books and articles are available detailing aspects of this useful investigational tool. For example, operational principles of, and procedures for use of, modern cytometers are set forth in "Practical Flow Cytometry" by Howard M. Shapiro, the contents of which are hereby incorporated by this reference. Flow cytometry is currently used in a wide variety of applications including hematology, immunology, genetics, food science, pharmacology, microbiology, parasitology and oncology.

In flow cytometry, microscopic particles entrained in a carrier fluid are typically arranged in single-file inside a core stream using hydrodynamic focusing. The particles are then individually interrogated by an optical detection system. The interrogation typically includes directing a light beam from a radiation source, such as a laser, transversely across the focused stream of single-file particles. The light beam is scattered by each particle to produce a scatter profile. The scatter profile may be analyzed by measuring the light intensity at both small and larger scatter angles. Certain physical and/or chemical properties of each particle can then be determined from the scatter profile.

It is also known to apply a biological label, such as one or more fluorescent tag, to selected particles of interest prior to processing such particles in a cytometer. For example, particles such as blood cells can be "tagged" with fluorescent molecules or small beads by using conjugated monoclonal antibodies. The wavelength of a radiation source (typically a laser), is matched to the excitation wavelength of the fluorescent tag. The tagged particles fluoresce in the cytometer, in accordance with a phenomena widely known as Stokes-shift, when excited by a laser beam. The fluorescence given off by the excited tag can be detected by an appropriately configured detector, which is conventionally mounted transverse to the path of the particles in the interrogation portion of the cytometer. Therefore, cells tagged with fluorescent markers can be easily detected for counting, or other data manipulation.

Unfortunately, flow cytometers are undesirably complex and expensive pieces of equipment. Care must be taken to ensure the machine is set up correctly, properly calibrated, and that care is taken to align optics and radiation sources, such as lasers. It would be an advance to provide a robust, inexpensive apparatus that can be used to promote single-file particle travel through an optically based interrogation zone to promote rapid processing of a plurality of different particle-bearing fluid samples.

SUMMARY OF THE INVENTION

The invention may be embodied to provide a microfluidic interrogation apparatus or system. A preferred embodiment includes indexing structure, a source of stimulation radiation, adjustment means, sensor means, and at least one photodetector. An interrogation apparatus may be used to detect, sort, quantify, and/or qualify particles of interest that are carried in a sample of fluid. Embodiments generally are used in combination with a microfluidic device, such as a removable cassette. Preferred embodiments are structured to fit inside an envelope having a volumetric size of less than about 6 inches by about 9 inches by about 3 inches.

A preferred microfluidic cassette is of the type arranged to urge particles of interest through the interrogation aperture in a substantially single-file arrangement. The source of stimulation radiation is generally structured to emit radiation as a beam oriented for propagation of stimulation radiation in a particular direction, such as though an interrogation aperture of a cassette. At least a first photodetector is disposed in an operable position to detect Stokes-shift emission radiation from a particle passing through the interrogation aperture.

Operable indexing structure is effective to hold a microfluidic device, such as a cassette, at an installed position such that an interrogation aperture of the cassette is urged near to a desired location. An exemplary indexing structure includes a first pin structured for reception in a first socket of a cassette. In such case, the first pin and first socket cooperate to cause the first socket of an installed microfluidic device to be positioned at a known X-Y coordinate with respect to the interrogation apparatus. The exemplary indexing structure may further include a second pin structured for reception in a second socket of the microfluidic device. The second pin and second socket may then cooperate to cause the installed cassette to be positioned at a known angular orientation with respect to the first pin.

Workable adjustment means is broadly defined as any structure or mechanism operable to refine relative alignment between the interrogation aperture and stimulation radiation beam. The adjustment means changes disposition of one or more element, from an initially installed position, to maximize beam propagation through the interrogation aperture. Desirably, an adjustment means is automated. However, it is within contemplation that an adjustment means includes manual manipulation by a user of the interrogation apparatus.

One operable adjustment means includes steering means configured to change the disposition of a path of propagation of the stimulation radiation beam. By steering means, it is intended to encompass any structure effective to change an orientation angle of the beam. An operable steering means includes a mirror affixed to a steering table. Another operable adjustment means includes an X-Y displacement means structured to move the stimulation beam into alignment with the interrogation aperture of the microfluidic cassette. Alternatively, adjustment means may include X-Y displacement means structured to move the microfluidic cassette into alignment with the stimulation radiation beam.

Desirably some sort of sensor means is disposed to provide steering feedback to the adjustment means. Broadly, a sensor means is intended to encompass any structure or system capable of providing feedback information to facilitate relative alignment between a stimulation radiation beam and an interrogation aperture. A workable sensor means can include an optical diode disposed on an exit side of the interrogation aperture with respect to the stimulation radiation beam. An alternative sensor means may include a photodetector disposed on an entrance side of the interrogation aperture with respect to the stimulation radiation beam.

An operable source of stimulation radiation includes a laser directed through a filter element and a focusing lens to form a coherent beam. It is preferred for the coherent beam to have a characteristic cross-section size that is smaller than a characteristic size of a cooperating cross-section of the interrogation aperture. In certain cases, a restricting orifice may be disposed in a path of the beam and upstream of the aperture. Such an orifice can be structured to resist passage of fringe radiation to improve coherence of the beam downstream of the orifice.

One embodiment includes a laser directed through a filter element and a focusing lens to form a coherent beam. A steerable first mirror is disposed downstream of the lens to redirect the beam for reflection from a second mirror and into an interrogation aperture of an installed microfluidic cassette. In such case, the second mirror is a dichroic mirror. This embodiment is arranged such that Stokes-shift emission radiation from a particle disposed in the interrogation aperture may propagate along an emission radiation path through the second mirror for detection by a first photodetector. Embodiments may include a plurality of photodetectors, each such photodetector being associated with a mirror (or dichroic mirror) disposed in the emission radiation path and adapted to direct emission radiation from the emission radiation path toward a photodetector. Sometimes, a mirror element may be disposed upstream of the photodetectors and arranged to change a direction of propagation of the emission radiation path to permit compact assembly of the apparatus. Mirrors may be omitted in certain circumstances, depending upon orientation.

In another embodiment, a laser is directed through a filter element and a focusing lens to form a coherent beam. The beam is then directed for propagation through a first dichroic mirror and into an interrogation aperture. In this embodiment, the first dichroic mirror is structured and arranged such that Stokes-shift emission radiation from a particle disposed in the interrogation aperture may propagate along an emission radiation path for reflection from the first dichroic mirror and subsequent detection by a first photodetector.

A method of using an exemplary interrogation apparatus structured according to certain principles of the invention includes: installing a microfluidic device into initial registration with respect to the apparatus; adjusting a relative position of the device with respect to a stimulation radiation beam to minimize autofluorescence caused by impingement of the beam onto a portion of the device; processing a sample of particle-carrying fluid to detect Stokes-shift radiation from one or more particle of interest in the sample; and removing the microfluidic device from the apparatus. In the case where the apparatus further includes electrical circuitry adapted to cooperate with the microfluidic device to permit detection of Coulter effect phenomena due to travel of one or more particle of interest through said interrogation aperture, the method may also include simultaneously detecting Coulter effect phenomena and Stokes-shift emission while processing the sample.

DETAILED DESCRIPTION OF THE ILLUSTRATED EMBODIMENTS

The present invention provides an apparatus and method for performing flow cytometry. A preferred apparatus is structured to detect Stokes-shift emission radiation from particles of interest while using an optimized signal-to-noise ratio. Particles of interest may also be identified and/or quantified by detection of Coulter effect phenomena. Methods for use of such a detector are disclosed herein.

Figure 1:
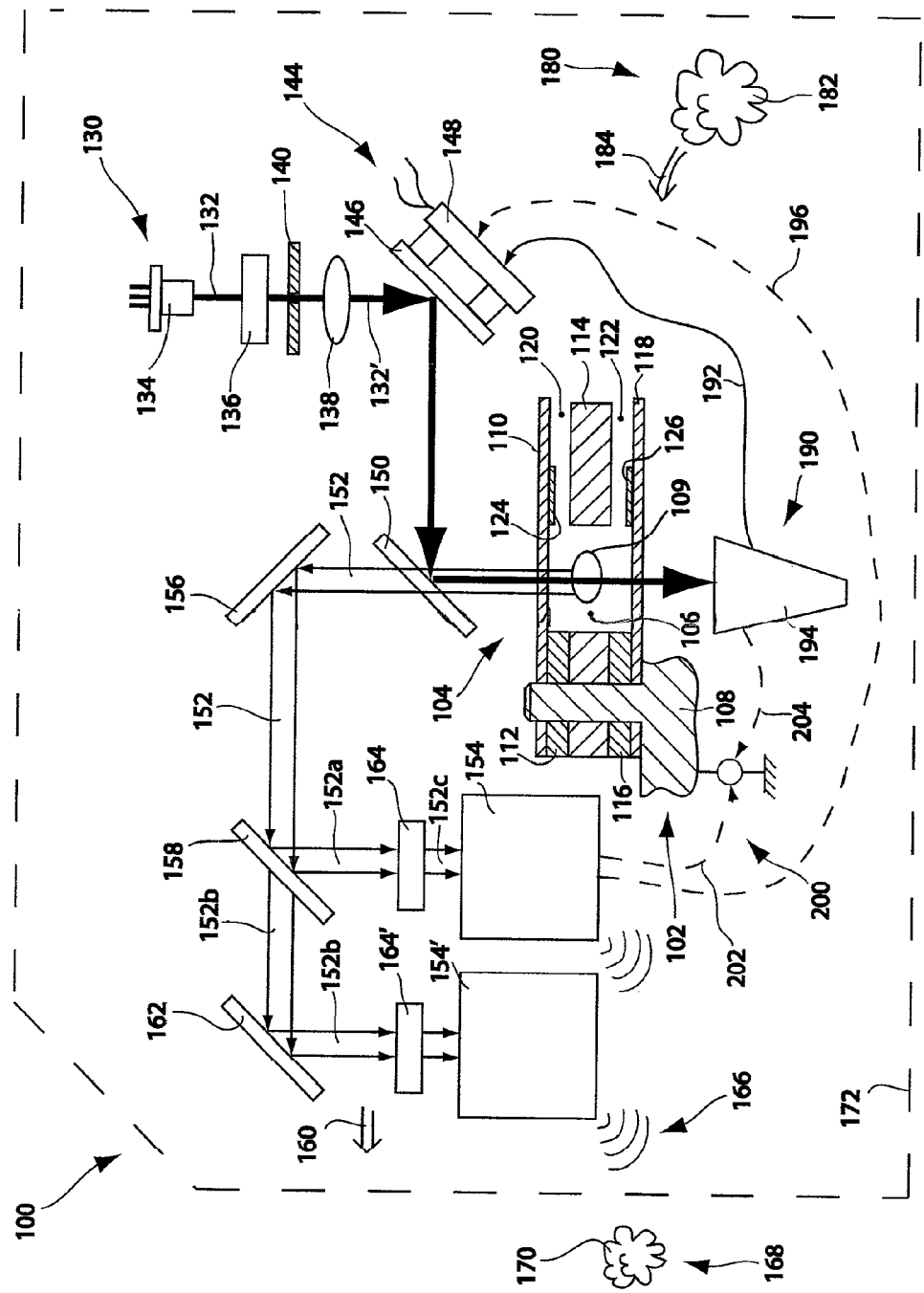
FIG. 1 is a schematic of a first exemplary embodiment structured according to certain principles of the instant invention.

FIG. 1 illustrates general principles of construction for an operable interrogation device, generally 100, structured according to certain principles of the instant invention. Interrogation device 100 includes indexing structure, generally indicated at 102, effective to hold a microfluidic device (or cassette), generally 104, at an installed position such that an interrogation aperture 106 of the cassette 104 is urged near to a desired location. Illustrated indexing structure 102 includes alignment pin 108 sized to interface with a cooperating portion of a cassette 104 to establish an initial X-Y position of known structure of cassette 104 with respect to an initially installed location in engagement with interrogation device 100. Workable indexing structure may be arranged in a variety of ways that will be apparent to one of ordinary skill effective to form an interface between alternative positioning structure of a cassette 104 and an interrogation device 100 effective to establish an installed position of the cassette within a desired range of precision. A clamp mechanism (not illustrated) is conventionally provided to hold a cassette 104 in engagement with a portion of indexing structure 102.

An operable and cooperating microfluidic cassette 104 is generally of the type that is arranged to urge particles of interest 109 through an interrogation aperture 106 in a substantially single-file arrangement, as will be further explained in some detail below. In brief, exemplary cassette 104 includes a top cap layer 110, a top channel layer 112, an interrogation layer 114, a bottom channel layer 116, and a bottom cap layer 118. A top channel 120 is conveniently formed by removing material from top channel layer 112. A bottom channel 122 is similarly conveniently formed by removing material from channel layer 116. Top channel 120 is disposed in fluid communication through interrogation aperture 106 to bottom channel 122. In general, one or more surface electrode(s) 124, 126, is/are or may be carried between the various layers of a microfluidic device, such as cassette 104, to make contact at one or more desired location with fluid flowing in the channels 120, 122.

An interrogation device, or apparatus, 100 includes a source of stimulation radiation, generally indicated at 130, that desirably is structured to emit radiation as a beam 132 oriented for propagation of stimulation radiation in a particular direction. A currently preferred source of radiation 130 includes a laser 134 configured to pass stimulation radiation beam 132 through a filter 136 and a focusing lens 138 to form a coherent beam 132' having a desired small characteristic size (e.g. diameter). In certain cases, an optional restricting orifice 140 may be included to resist propagation of fringe light downstream of the orifice 140, and thereby improve coherence of the beam 132'.

It is currently preferred for the characteristic size of a beam 132' to be slightly less than the characteristic size of an interrogation aperture 106, to permit the beam 132' to pass cleanly through the aperture 106 without generating a significant amount of autofluorescence of structure of a cassette 104 (preferably none). Sometimes such may be characterized as to maximize beam propagation through the aperture 106. In addition to generating autofluorescence, impingement of a beam edge onto structure of a microfluidic device, such as cassette 104, can also undesirably cause light scattering from surface roughness, reflection from constituent layer surface boundaries, and other irregularities. Therefore, it is desirable for the beam 132' to be in sufficient alignment with an axis of, and pass cleanly through, the aperture 106. However, it is desirable for beam 132' to substantially fill the cross-section of interrogation aperture 106, at least to an extent sufficient to resist allowing a particle of interest 109 to pass through the aperture 106 without being sufficiently bathed in stimulation radiation 132' as is required for that particle to undergo an associated detectable Stokes-shift emission of radiation.

Desirably, an interrogation device 100 includes some sort of structure or mechanism arranged to fine-tune the alignment and/or disposition of a beam 132' relative to an aperture 106 of a microfluidic device 104 from an initially installed position of that device 104. For that reason, various adjustment structures, or mechanisms, generally 144, may be provided to refine relative positions between an interrogation aperture 106 and a stimulation radiation beam 132' to maximize beam propagation through the aperture 106. With reference still to FIG. 1, one such adjustment structure includes a steering mirror 146 carried on a steering table 148. A workable steering table 148 includes a commercially available piezo-actuated table. One such table is available on-line from Edmunds.

An operable adjustment structure 144 generally illustrated in FIG. 1 may sometimes be made reference to as a steering means. An operable steering means can be manipulated to reflect stimulation radiation beam 132' from a mirror 150 to pass cleanly through aperture 106 (of course in the absence of a particle 109). Illustrated mirror 150 is a dichroic mirror selected for its ability to reflect stimulation radiation and transmit emission radiation 152.

When stimulation radiation 132' encounters a particle of interest 109, the particle 109 produces Stokes-shift emission radiation 152 that propagates in substantially all directions. For convenience, a portion of such emission radiation 152 is indicated in FIG. 1 as a beam bounded between parallel arrows. A photodetector, such as photodetector 154, can be positioned directly to acquire the emission radiation beam 152. A workable photodetector can include a photomulitplier tube (PMT) or an avalanche photodiode (APD).

As illustrated in FIG. 1, the propagation path for beam 152 can be changed by reflection from a path-folding mirror 156. Such an arrangement can produce a more compact interrogation apparatus 100, for example. In any case, a plurality of sequential photodetectors can be disposed to interrogate portions of the emission beam 152. As illustrated, dichroic mirror 158 reflects a beam 152$a$ including wavelengths of a certain spectra. A remaining portion 152$b$ passes through mirror 158, and can be further parsed by additional dichroic mirrors and associated photodetectors, as indicated generally by arrow 160. As illustrated, mirror 162 is associated with photodetector 154' to direct a portion of emission radiation 152$b$ for detection by detector 154'. Mirror 162 could be either a conventional reflecting mirror, as illustrated, or a dichroic mirror, as desired. Sometimes, a filter, such as filters 164, 164' may be disposed in the path of emission radiation, to restrict the signal(s) received by the associated photo detector(s). For example, filter 164 removes undesired wavelengths and permits only a resulting subset of wavelength(s), indicated by radiation beam 152$c$, to impinge onto photodetector 154.

Data about received and detected radiation is communicated, generally indicated at 166, to an analysis platform of some sort, generally indicated at 168. An analysis platform 168 is typically used to manipulate data received from one or more photodetector, among other functions. The communication 166 from a photodetector can be by way of any desired mechanism, including wireless transmission or conventional wired transmission.

Exemplary workable analysis platforms 168 include a computerized hand-held device 170, such as an iPOD™, Palm Pilot™, smart phone, computer tablet, iPAD™, and fully integrated designs with color touch displays running operating systems like Linux, and the like, or more substantial platforms, such as a personal computer, mainframe, and the like. Desirably, an analysis platform 168 includes a processing device, memory in which to hold programmed instructions (software), and a display device, such as a CRT or digital display screen of some sort.

In a currently preferred embodiment, the analysis device 168 is incorporated into the envelope 172 defining device 100. A currently preferred envelope 172 defines a volumetric size of less than about 6 inches by about 9 inches by about 3 inches. Sometimes the interrogation device 100 may be battery operated. Other times, the device 100 may include a cord to obtain electrical power from a utility, such as a conventional wall outlet. In the latter case, the power cord is generally not included in consideration of the volume defined by envelope 172.

An analysis device 100 may also include assorted on-board utilities, generally indicated at 180. Operating structures or systems that may be included in utilities 180 include one or more of: structure to urge fluid flow through an installed microfluidic device 104, such as a vacuum source 182 that can be placed into communication 184 with a channel 120 or 122; and electrical detection circuitry that may be placed into communication with one or more electrode, such as electrode 124 or 126 (e.g. by way of an edge connector); among other operating structures or systems. Of course, electrical interrogation circuitry is also desirably placed into communication with the analysis platform 168 to incorporate evidence of Coulter-effect phenomena into cytometric data analysis.

As previously mentioned, it is desirable to orient the stimulation beam 132' with respect to the aperture 106 to avoid, or at least reduce and desirably minimize, undesired autofluorescence and thereby improve the signal-to-noise ratio obtained by interrogation device 100. One adjustment structure 144 effective to accomplish such includes the aforementioned steering mirror 146. Steering mirror 146 illustrates only a first exemplary way to adjust the beam 132' with respect to an aperture 106.

Desirably, some sort of feedback is provided to inform a user, or an automated system, when alignment has been sufficiently accomplished. With reference to FIG. 1, a feedback sensor, generally indicated at 190, may be configured to provide a feedback signal 192 for use in optimizing aim of beam 132' by way of steering mirror 146. An operable feedback sensor includes an optical diode 194. Desirably, optical diode 194 also operates as a light sink, or such light sink is provided by a different element. In any case, it is generally good practice to control stray (e.g. reflected) light inside device 100.

An optical diode 194 is an operable sensor to detect intensity of radiation downstream of aperture 106. The signal detected by sensor 194 may be maximized to indicate desired clean propagation of beam 132' through aperture 106. Alternatively, a signal from a photodetector, e.g. 154, can sometimes be used to accomplish the same result. In the latter case, an autofluorescence signal detected by detector 154 would be minimized to indicate desired relative alignment between beam 132' and aperture 106. In the latter case, an alternative feedback signal 196 can then be applied as a feedback loop variable to drive an adjustment structure or mechanism to effect a relative position between beam 132' and aperture 106. It is within contemplation that both stimulation radiation and autofluorescence emission radiation may be incorporated in a feedback loop to control relative position of a beam 132' and aperture 106.

It is also within contemplation to adjust the position of an aperture 106 with respect to a beam 132'. An operable alternative adjustment structure 144 includes an X-Y adjustment system, generally indicated at 200. Adjustment system 200 is effective to move a cassette 104 to fine-tune an initially installed position. Moving the cassette 104 also moves aperture 106 with respect to the beam 132'. One or more of feedback signals 202 and 204 may be incorporated into a displacement-adjustment control feedback loop. A workable X-Y adjustment system includes an X-Y motion table that may be driven manually, or by one or more motor or piezo actuator. It should be noted that, although it is preferred for a relative position adjustment and optimization using a signal maximization or minimization procedure to be automated, it is workable for a user to perform a fine-tuning relative alignment manually, using an appropriate feedback signal.

An exemplary automated system is effective to automatically optimize beam propagation through an interrogation aperture subsequent to receiving an installed cassette. Such a system may, for nonexclusive example, optimize (e.g. by way of either or both of maximizing a feedback signal or minimizing a feedback signal) as a portion of an automated test sequence. The optimization routine can be included as a pre-programmed software step or process. In such case, a user may install a cassette, and then activate a test sequence; perhaps by pressing a button or the equivalent, and allow the automated equipment to perform the optimization process.

The automated test sequence then will automatically adjust the relative position between beam and aperture before urging flow of sample fluid.

Figure 2:
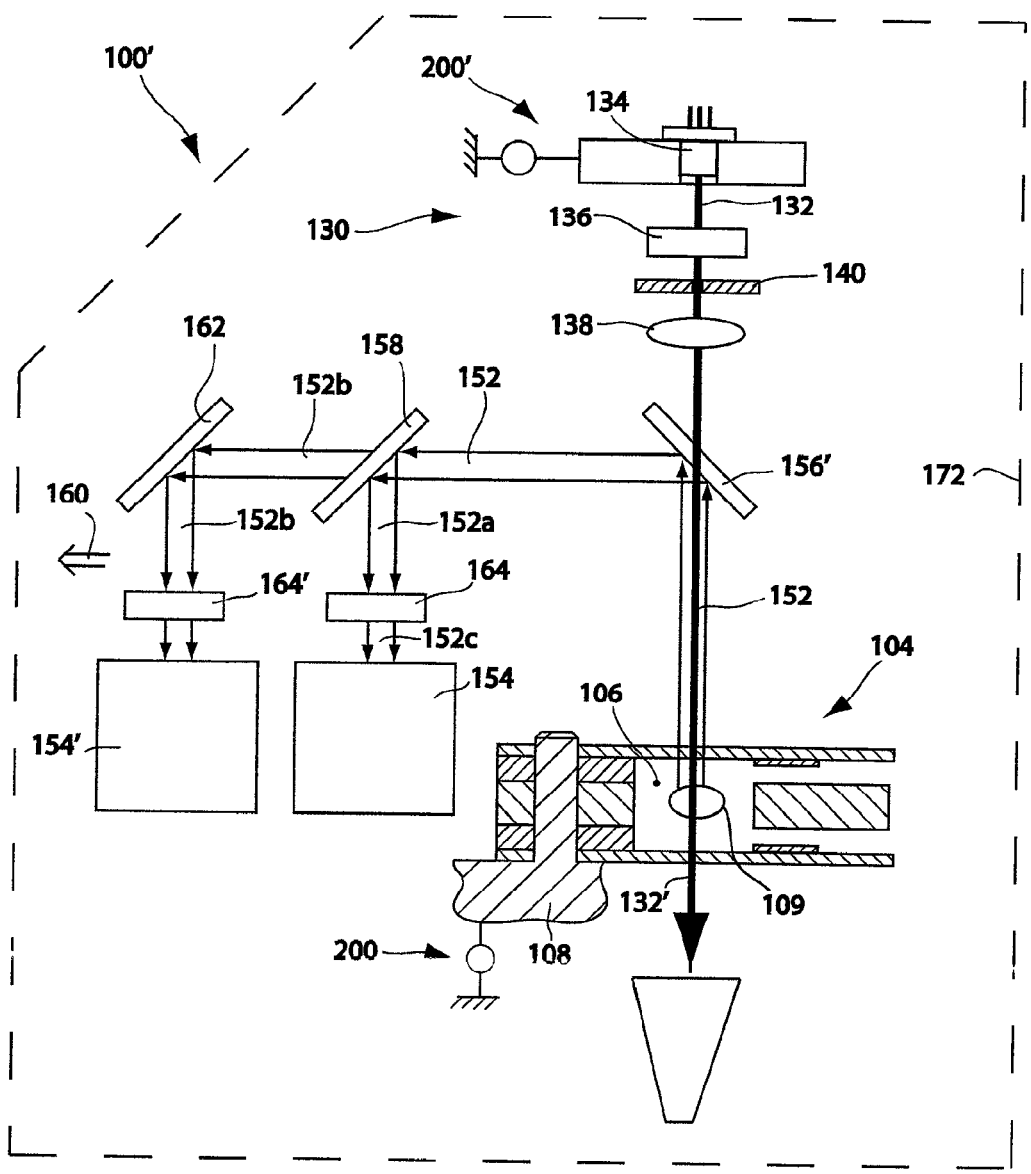
FIG. 2 is a schematic of a second exemplary embodiment structured according to certain principles of the instant invention.

An alternative microfluidic interrogation device, generally 100', is illustrated in FIG. 2. The emphasis of FIG. 2 is illustration of an alternative path for stimulation radiation 132, and it should be recognized that FIG. 2 omits certain subsystems and structures that are present in FIG. 1. As depicted in FIG. 2, stimulation radiation 132 from a source 130 may be directed toward an interrogation aperture 106 in a substantially straight line. Stimulation radiation beam 132' passes through dichroic mirror 156'. As was the case in embodiment 100, emission radiation is depicted as a beam 152. Duplicated downstream elements and other elements of device 100' are labeled in accordance with similar elements previously described with reference to embodiment 100.

Importantly, embodiment 100' in FIG. 2 illustrates an X-Y adjustment system 200' adapted to displace the stimulation radiation source 130 relative to the aperture 106. It is also within contemplation that adjustment system 200' may also, or alternatively, change an angle of propagation of beam 132 to avoid, or at least reduce and desirably minimize, undesired autofluorescence and thereby improve the signal-to-noise ratio obtained by interrogation device 100'. For example, one or more actuator, such as a piezo actuator or motorized link, could be disposed to rotate mounting structure for, and thereby adjust the angle of discharge of, laser 134.

Similar to embodiment 100, interrogation device 100' may alternatively, or also, include an X-Y adjustment structure such as is generally indicated at 200. Adjustment system 200 is effective to move a cassette 104 from an initially installed position in a fine-tuning operation, and consequently move aperture 106 with respect to the beam 132'.

Figure 3:
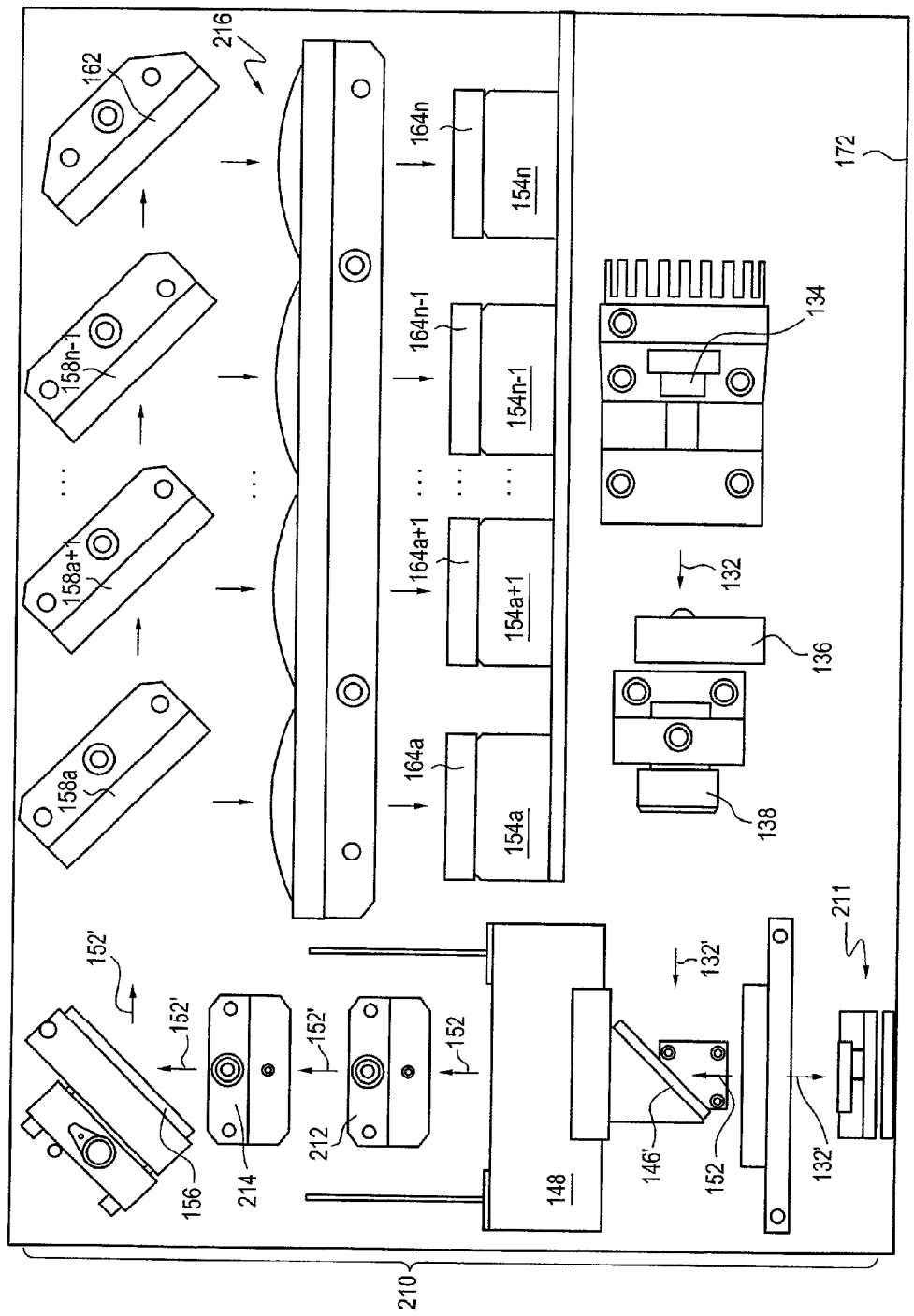
FIG. 3 is a side view in elevation of a currently preferred embodiment, partially assembled.

FIG. 3 illustrates selected elements of a workable and compact packaging arrangement for an interrogation device, generally indicated at 210. Embodiment 210 desirably fits into the preferred envelope 172. Straight-shafted arrows indicate direction of propagation of radiation.

Elements of embodiment 210 in common with previously disclosed embodiments are generally identified with similar numerals. Holding structure, to hold a cassette, such as cassette 104, in an initial installed position, is generally indicated at 211. Repeated elements are indicated by subscript. In the illustrated embodiment, subscript a=1, and subscript n=4. It must be appreciated that n could be a larger number; generally controlled by available technology and corresponding elements having desired discrimination capabilities.

Of note, steering mirror 146' is a dichroic mirror, which reflects stimulation radiation beam 132' (downwardly as drawn), toward an interrogation aperture in an installed microfluidic device (e.g. cassette 104), and allows emission radiation 152 to pass through in a straight line for detection by photodetectors $154_{a-n}$. As illustrated, an optional filter 212 and/or focusing lens 214 may be included. Subsequent to filtering, emission radiation beam 152 is identified as beam 152'. A plurality of optional focusing lenses is generally indicated at 216.

Figure 4:
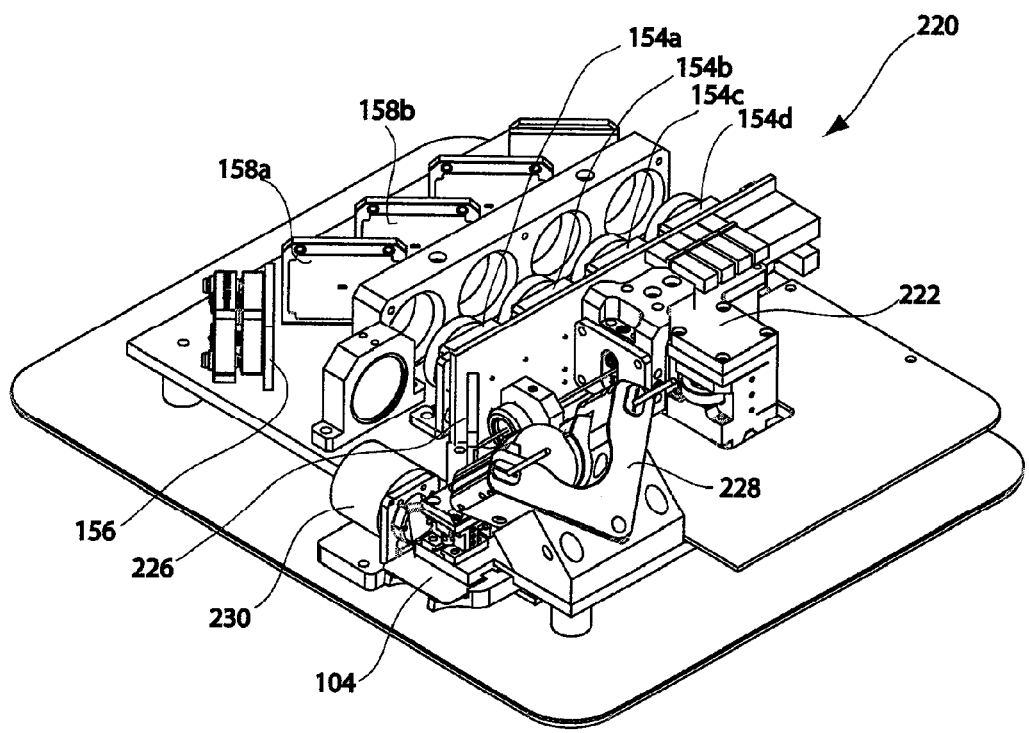
FIG. 4 is a view in perspective of a currently preferred embodiment, partially assembled.

With reference now to FIG. 4, another alternative embodiment structured to apply stimulation radiation to an interrogation aperture is illustrated, and is generally indicated at 220. Again, elements of embodiment 220 in common with previously disclosed embodiments are generally identified with similar numerals. Importantly, stimulation radiation is directed from laser assembly 222, through dichroic mirror assembly 226 to steerable mirror assembly 228, which directs stimulation radiation down into an interrogation aperture of a microfluidic device, such as cassette 104. Emission radiation propagating up from the interrogation aperture is reflected from the mirror element of assembly 228 through the dichroic element of assembly 226 and toward the path-folding mirror 156 for detection by the photodetectors $154_{a-d}$. A motor and cam assembly 230 may be provided to clamp a microfluidic device 104 in engagement with indexing structure.

Figure 5:
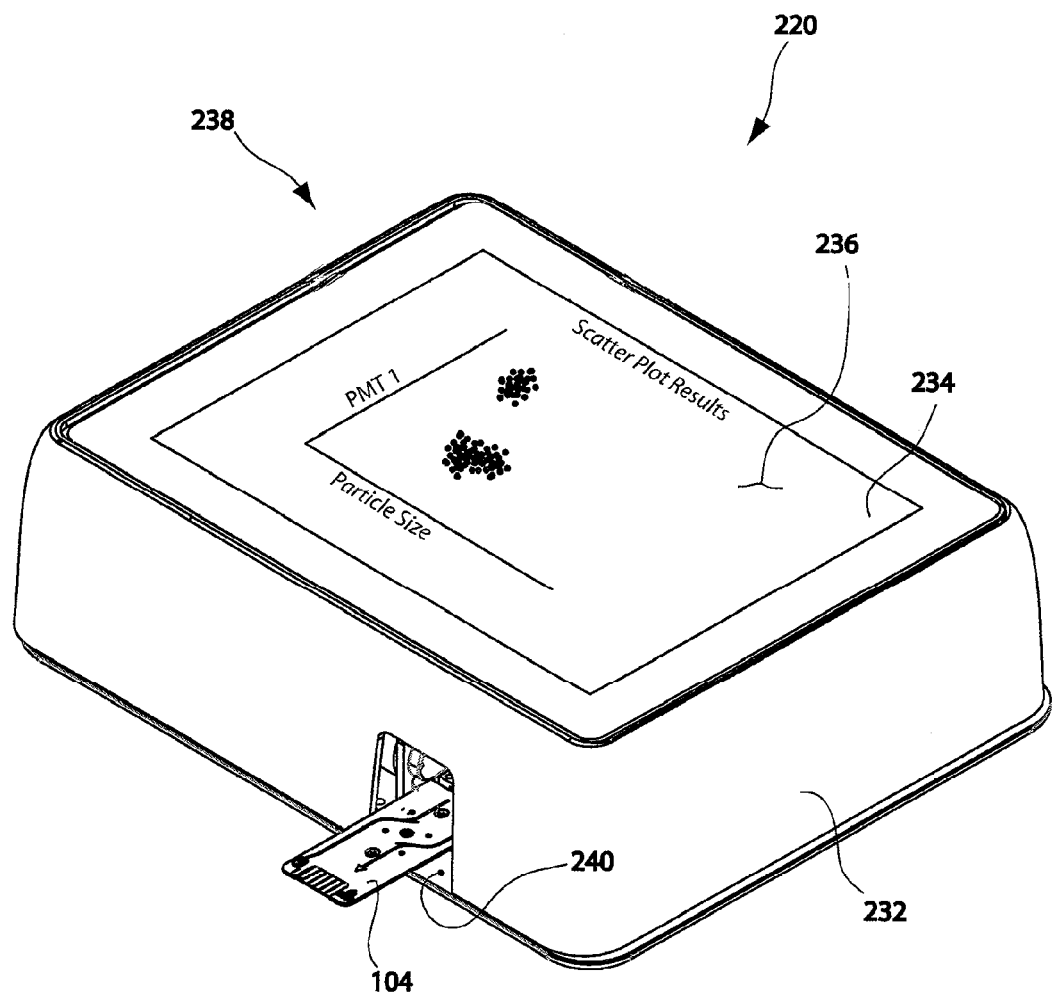
FIG. 5 is a view in perspective of a preferred embodiment.

With reference now to FIG. 5, which is illustrated in approximately the same frame of visual reference as FIG. 4, housing 232 of apparatus 220 is desirably structured to fit within the preferred envelope 172. A visual display 234 presents a surface 236 that indicates relevant data, generally 238. Data 238 may nonexclusively include one or more of; total count of designated particles; particle count per unit volume; type and/or size of particle; number of each particle type and/or size; etc. A cassette installation port 240 is structured to accept a microfluidic device 104 at an initially installed position.

Figure 6:
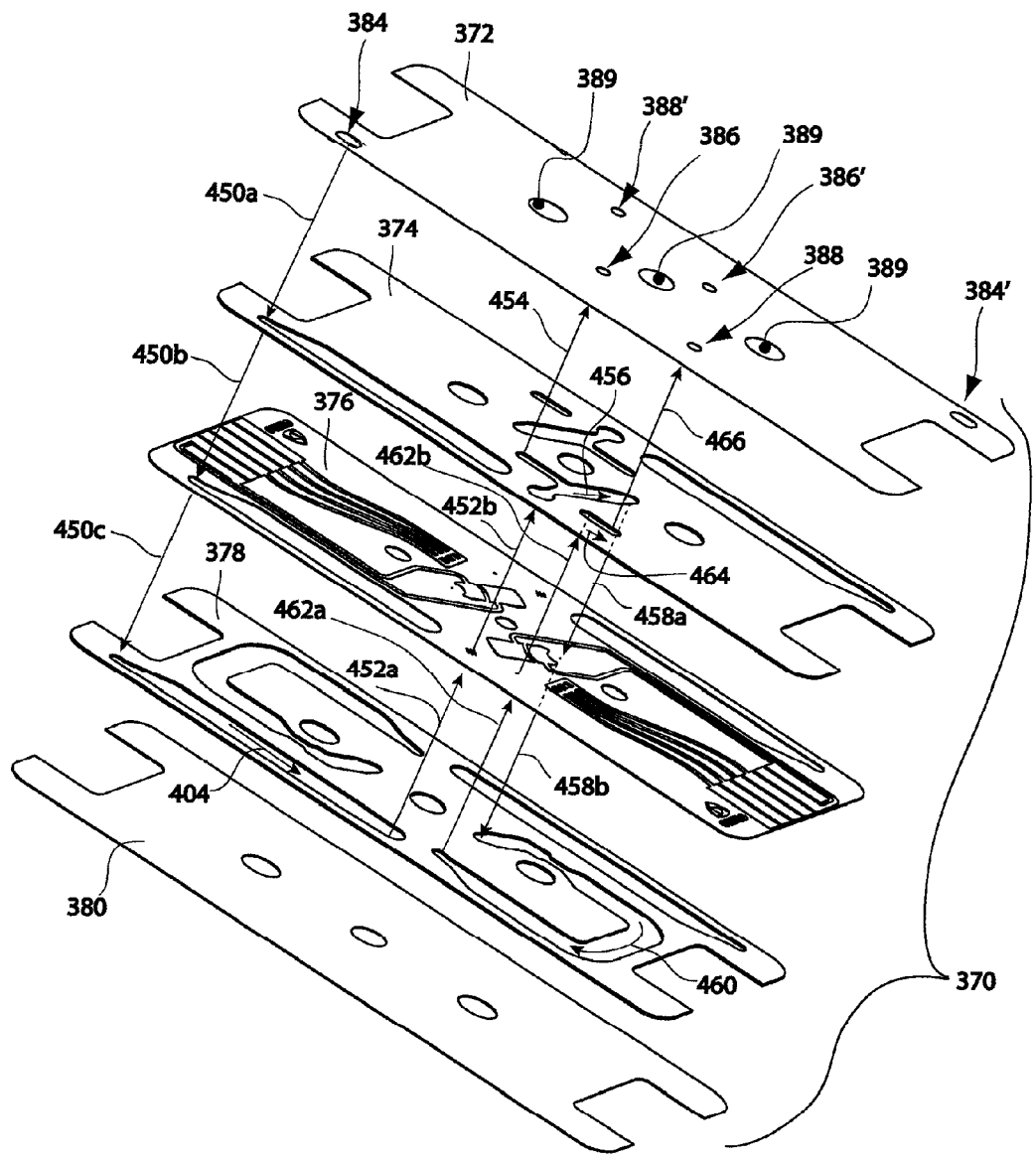
FIG. 6 is an exploded assembly view in perspective of a currently preferred cassette for use in certain embodiments of the invention.

Elements of a currently preferred microfluidic device, or cassette, generally 370, which can be used in accordance with certain principles of the invention, are illustrated with reference to FIGS. 6-10. An exemplary such cassette 370 may be assembled from a plurality of thin film layers that are stacked and bonded together to form a multilayer cassette. With reference to FIG. 6, cassette 370 includes top cap layer 372, top channel layer 374, interrogation layer 376, bottom channel layer 378, and bottom cap layer 380.

The currently preferred top cap layer 372 and bottom cap layer 380 may be made from 0.005" thick transparent polyester film. Desirably, the cap layers 372, 380, and at least a portion of the interrogation layer 376, are structured to cooperate for operable transmission of radiation (e.g. light 156) through the cassette 370. It is preferred to generally minimize the amount of autofluorescence inherent in a cap layer, because such autofluorescence represents background noise, and reduces a signal-to-noise ratio for the interrogation system 100.

Workable channel layers 374 and 378 may be made from 0.010" thick double-sided acrylic based adhesive film stock. In such case, the center carrier layer may be 0.007" thick polyester film with 0.0015" thick adhesive coated on each side. A currently preferred interrogation layer 376 may be made from an assortment of materials, depending upon the intended use for the particular sensor that will be constructed. A clear 0.005" thick polyester film may be used for sensors structured to interrogate impedance alone, or in combination with optically-based interrogation. It is preferred (although not required) to employ an opaque polyamide film for sensors structured to interrogate impedance and fluorescence (or just fluorescence). In certain cases, an opaque film layer inherently resists transmission of undesired radiation toward a Stokes' shift detection sensor. However, in a arrangement such as the embodiment illustrated in FIG. 1, it is preferred to either provide an interrogation layer 376 that inherently has a low autofluorescence, or to avoid impinging stimulation radiation onto that layer.

Illustrated cassette 370 is a two-ended arrangement structured to provide duplicated structure forming first and second sensors on the same removable and reversible cassette 370. For clarity, the duplicated structures included in the illustrated second sensor and designated by numeral are indicated with a prime. The illustrated arrangement permits associating the cassette 370 at a first orientation with an interrogation apparatus, running a first test, then removing and reversing the cassette 370 to interface with the interrogation device at a second orientation to perform a second test. The first and second tests may be the same type of test, or different tests, performed on different fluid samples. It is within contemplation that the first and second tests may not be the same, and may also be performed on at least a portion of the same fluid sample. For example, fluid may be passed through one sensor arrangement to a common storage chamber before being passed through a second, or subsequent, sensor arrangement on a single alternatively structured cassette. It is within contemplation to provide a multi-ended arrangement providing a further increased number of sensors (e.g. 3, or 4, or more) on the same cassette, or cartridge. A single-ended cassette is also within contemplation.

With continued reference to FIG. 6, top cap layer 372 provides a sample loading port 384, a vent 386, and a vacuum application port 388. A plurality of over-size alignments holes 389 are also illustrated. Alignment holes 389 are over-sized to provide clearance for other precise alignment structure during assembly of the cartridge 370. Alternative precision alignment structure may be provided for certain layers, such as 372, 374, 378 and 380, and can enforce consistent orientation of a cassette with respect to an interrogation apparatus. For example, one or more cassette edge can be formed with precision relative to an interrogation aperture, and the edge(s) may be aligned with stop structure of an interrogation apparatus. Certain alignment structure used primarily for assembly may be redacted from the finished cassette during a manufacturing step. Also, in certain embodiments, vent ports 386 are not included.

Figure 7:
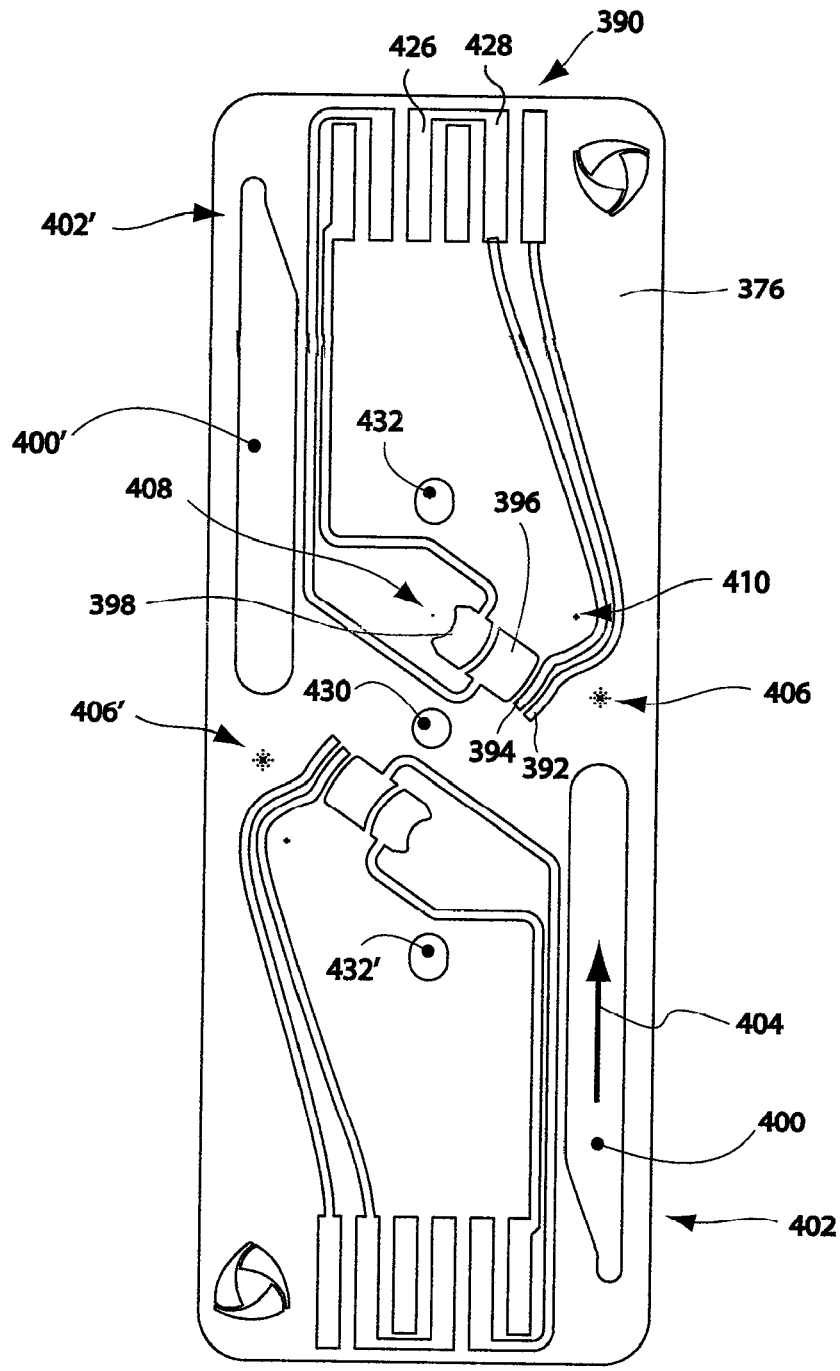
FIG. 7 is a top plan view of an interrogation layer of the cassette in FIG. 6.

With reference now to FIG. 7, interrogation layer 376 carries a plurality of surface contact electrical pads, generally indicated at 390. While alternative deposition of conductive material is operable, it is currently preferred to print the contact pads 390 and other electrically conductive traces and structures using electrically conductive ink and a web-based screen printing process that lends itself to mass production.

As illustrated in FIG. 7, interrogation layer 376 carries a first driving electrode 396 and a first detection electrode 398. A plurality of apertures and channels are removed from the film forming interrogation layer 376. As illustrated, a partial length channel 400 is disposed to receive a fluid sample for interrogation. The sample is typically loaded at proximal end 402, and flows in the direction indicated by arrow 404, toward debris filter 406. An exemplary debris filter resists passage of undesired particulate matter toward interrogation aperture 408. It is currently preferred to laser drill a plurality of small apertures in combination to form a sort of screen-like debris filter 406. An additional aperture structure includes fluid exit vent 410. Desirably, exit vent 410 is structured to permit application of vacuum to cause fluid flow through passages in the cassette 370, and to apply capillary attraction to resist flow of fluid beyond the vent 410, itself.

Figure 8:
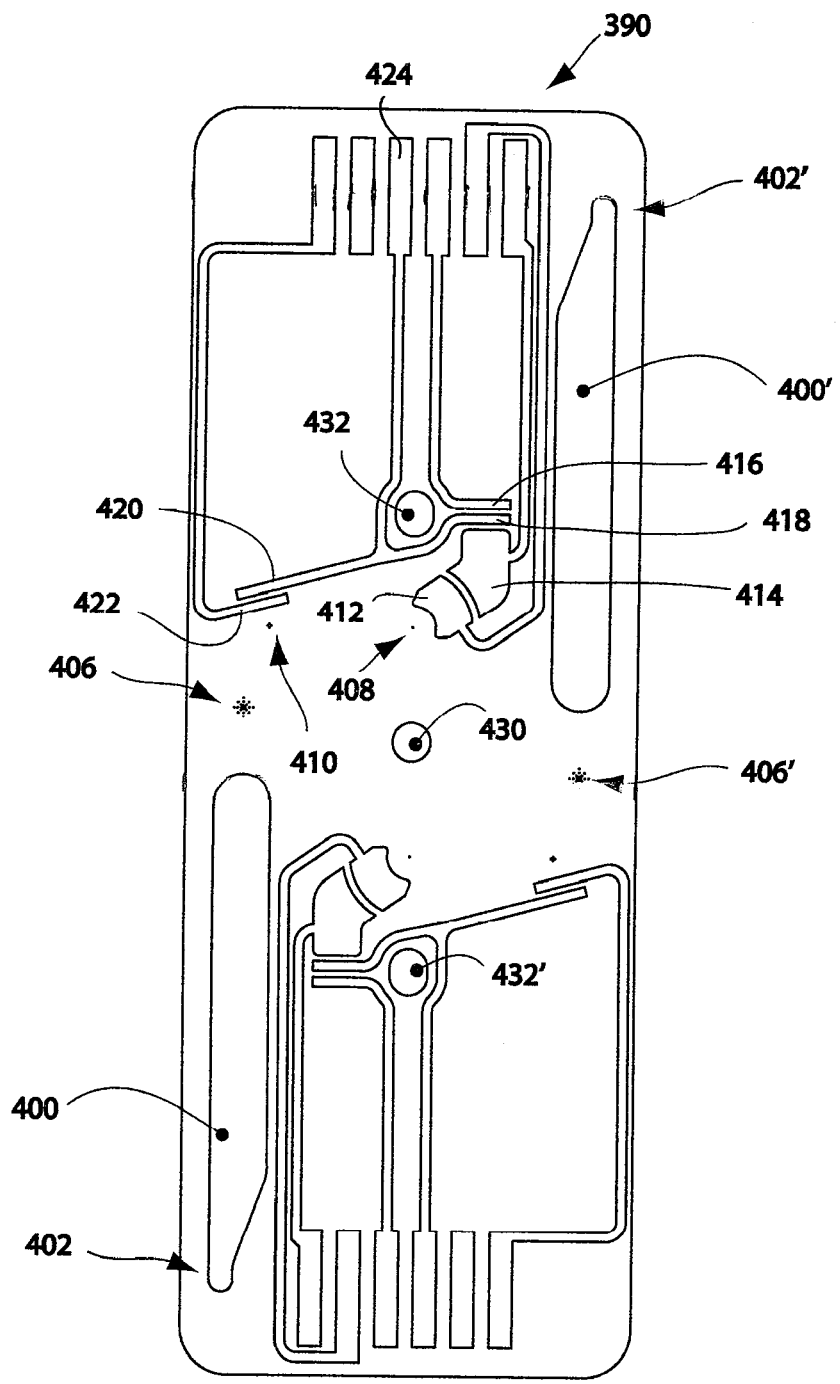
FIG. 8 is a bottom plan view of the interrogation layer in FIG. 7.

With particular reference to FIG. 8, the other side of interrogation layer 376 includes additional electrical contact pads, generally 390. In the illustrated embodiment, the electrical contact pads 390 disposed on one side are not disposed in electrical communication with electrical contact pads 390 on the other side, although such may be convenient in certain cases. Electrically conductive traces extending from the contact pads are configured to provide a second interrogation electrode 412 and a second driving electrode 414.

Still with reference to FIG. 8, a first trigger electrode 416 and a second trigger electrode 418 are disposed down stream of second detection electrode 412 and second driving electrode 414 and may therefore detect a fluid flow arrival boundary. Such an arrangement permits trigger electrode 416 and trigger electrode 418 to operate as an electrically-based trigger that is inherently tripped by a fluid flow boundary disposed at a known channel location, and can be used to begin data collection during the test of a fluid sample.

A third trigger electrode 420 and a fourth trigger electrode 422 are also illustrated in FIG. 8 as being disposed down stream of second detection electrode 412 and second driving electrode 414 and may therefore cooperate to detect a fluid flow arrival boundary at a second channel location. This trigger is disposed near the vent aperture 410. Such an arrangement permits electrode 420 and 422 to operate as an electrically-based trigger that can be used to detect the "end of test" for a fluid sample, e.g. when using a "known volume" method with respect to the volume in channel 442 and disposed between two trigger or boundary detection locations. A single trigger electrode can also be use to detect "end of test", in certain circumstances.

For convenience, electrode surface contact pad 424 is in electrical communication with both of electrode 418 and 420, and can therefore be used to apply a common reference signal, such as ground. On the other side of layer 376, electrical contact pads including 426 and 428 are in electrical communication through a multi-branch arrangement. Branches may be severed during manufacture of a cassette and the resulting continuity between the pads may be used for several purposes. For non-limiting examples: in a continuity check to verify proper insertion of a sensor into engagement with a preferred interrogation device, and to identify a cassette as a certain type. A particular test may be automatically selected and applied by an interrogation apparatus based upon the continuity through the mesh and between two or more contact electrodes. It should be noted that certain sensors may be constructed having a different number of driving, detecting, verification, and/or trigger electrodes, or even none.

Illustrated layer 376 also includes a plurality of alignment apertures. Alignment aperture 430 is common to alignment structure used for both ends of the cartridge 370, and imposes an X-Y location at a known reference spot on the cartridge 370 with respect to a currently preferred interrogation apparatus. Alignment slot 432 imposes substantially only a rotational orientation of an installed cartridge 370 with respect to that X-Y location. Desirably, one of the apertures 430, 432 is slotted, and the other is not. Such an arrangement is effective to provide a complete rigid body constraint in a plane, and helps to avoid binding of the cassette during its installation into, or removal from, an interrogation device. The radius of illustrated round alignment aperture 430 is 0.050". The distance between the radii of alignment slot 432 is 0.025" and the radii are 0.050". Cooperating alignment pins in the preferred interrogation device have diameters of 0.1000", and the alignment pins of the preferred interrogation device are precision ground to a tolerance of ±0.0001". Planar orientation of the cartridge is typically enforced by other clamping structure associated with the preferred interrogation device.

Figure 9:
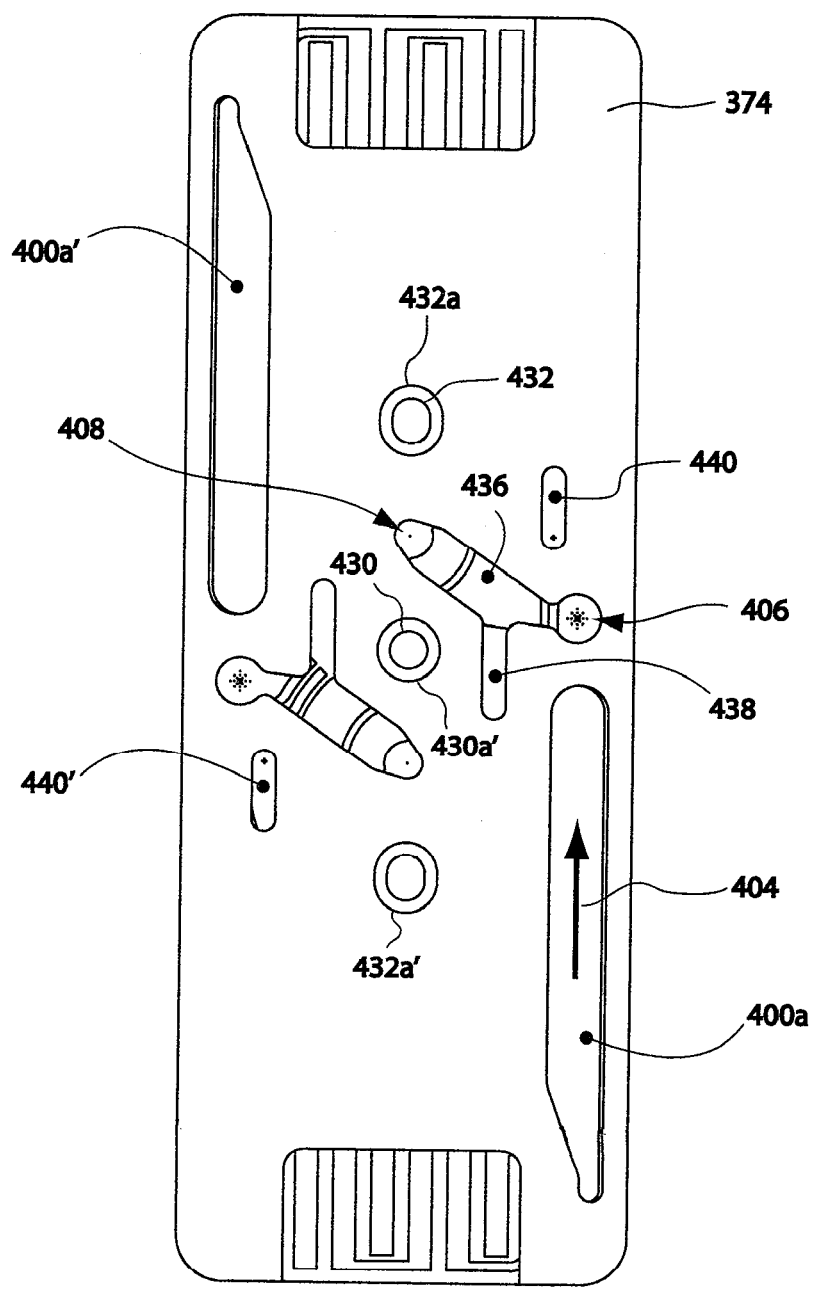
FIG. 9 is a top plan view of a partially assembled portion of the cassette in FIG. 6.

With reference now to FIG. 9, top channel layer 374 includes a plurality of channel structures. Partial-length fluid receiving channel 400*a* cooperates with channel 400 in layer 376 to permit introduced sample fluid to flow in the direction indicated by arrow 404. Bridge channel 436 transports fluid from debris filter 406 toward interrogation aperture 408. An optional dogleg channel portion 438 may communicate to an optional vent 386 (see FIG. 6) at the top of the cartridge 370, and facilitates loading a fluid sample into the cartridge 370. Buffer channel 440 communicates from exit vent 410 toward a vacuum port 388 (see FIG. 6) on top of the cartridge 370. Along with over-size apertures 389, alignment apertures 430*a* and 432*a* are also desirably pulled back during a manufacture step to avoid causing a potential structural interference with respect to alignment apertures 430 and 432 disposed in penetration though the interrogation layer.

Figure 10:
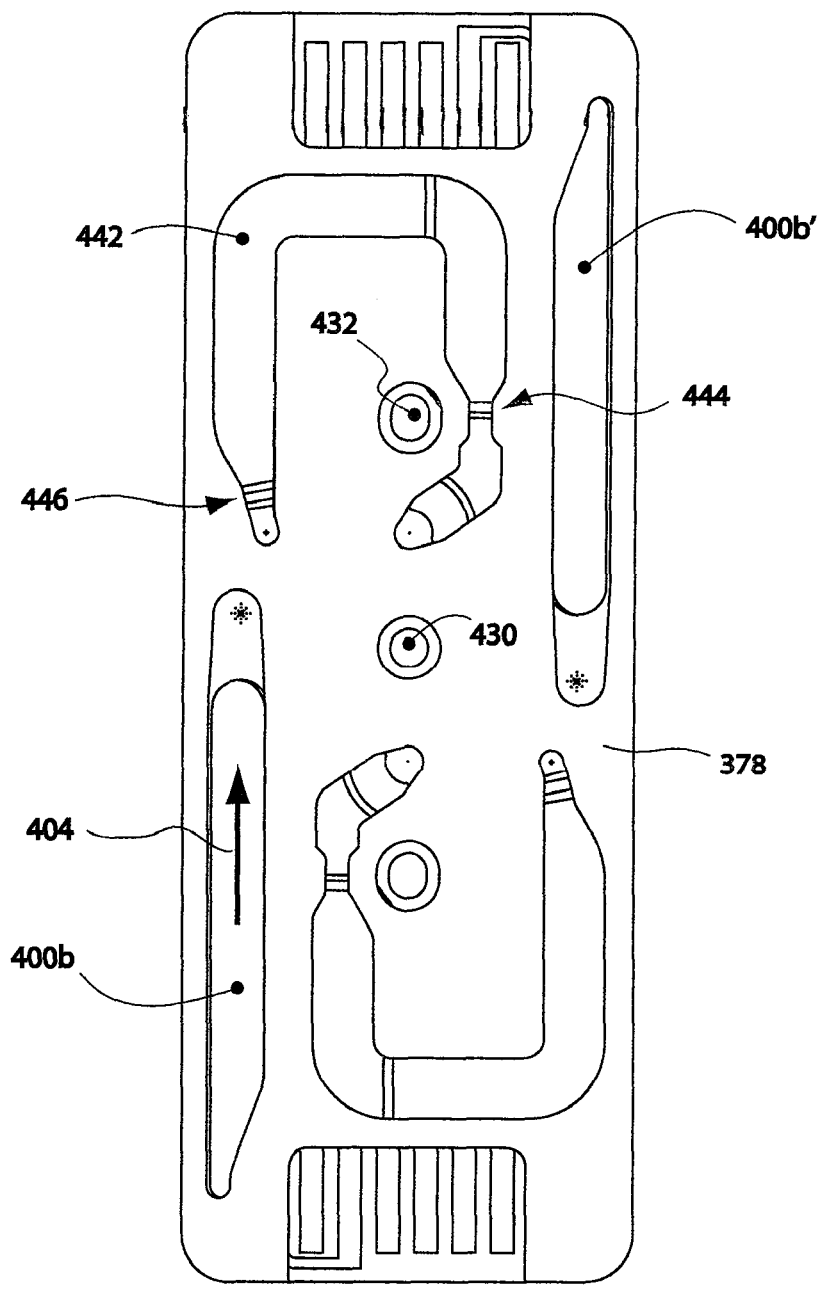
FIG. 10 is a bottom plan view of a partially assembled portion of the cassette in FIG. 6.

With reference now to FIG. 10, bottom channel layer 378 carries full-length sample receiving channel 400*b*. Channel 400*b* communicates introduced fluid underneath layer 376 to the bottom of debris filter 406. Channel 442 receives fluid downstream of interrogation aperture 408. In certain embodiments, a first electrically-based trigger, generally indicated at 444, is disposed near one end of the chamber formed by channel 442. A workable trigger may be formed between two dedicated electrodes, or sometimes between one dedicated electrode and a shared electrode. Sometimes, it is desirable for paired cooperating trigger electrodes (sometimes also called test electrodes) to be narrow and disposed as close together as possible. An electrode area can be fairly small (e.g. 0.025"×0.065") and the current printing process can easily maintain a 0.015" spacing between printed electrodes.

Illustrated trigger 444 in FIG. 10 is formed between electrodes 414 and 418 (see FIG. 8). A trigger at a location such as trigger 444 is operable as a "start" trigger, to begin collection of data during an interrogation of a fluid sample. It has been determined that a single impedance-detecting electrode, such as 418, cooperating with a source or driving electrode 414 is more reliable than a cooperating dedicated pair of electrodes 418, 416 disposed in very close association with a driving electrode such as 414.

A second electrically-based trigger, generally 446, may be disposed spaced apart from trigger 444 by a known volume provided by channel 442. Illustrated trigger 446 is formed by electrodes 420 and 422 (see FIG. 8). In certain cases, a second known volume may be defined by channel and aperture structure disposed between trigger 444 and an upstream trigger, such as may be formed between electrodes 292 and 294 (see FIG. 7).

Known volumetric trigger spacing and collection of data signals including a common time component or base, permit: starting and stopping test data collection; control for application of vacuum; confirmation of processing a desired sample volume; and calculation of volumetric rate of processing, among other capabilities.

With reference again to FIG. 6, the fluid flow path through cassette 370 will now be described. In one type of test, a sample is typically introduced to sample loading port 384 using a pipette instrument to accurately dispense a desired test volume, or sometimes a surplus volume. Entering fluid flow is represented by arrows 450*a*, 450*b* and 450*c*. Sample fluid then flows along a channel formed by channel portions 400, 400*a*, and 400*b* in the direction indicated by arrow 404. As indicated by arrows 452*a* and 452*b*, fluid flow through debris filter 406 to channel 436. Air may be passed out aperture 386, as indicated by arrow 454. During a test, fluid flows along channel 436 in the direction indicated by arrow 456. Fluid then flows through interrogation aperture 408 as indicated by partially hidden arrows 458*a* and 458*b*. Fluid flow in channel 442 is indicated by arrow 460. Fluid then flows through vent 410 as indicated by arrows 462*a* and 462*b*. Fluid then flows along channel 440 in layer 374, in the direction indicated by arrow 464, before potentially exiting vacuum port 388, indicated by arrow 466. In certain cases, channel 440 may provide a buffer volume to resist escape of fluid from a cartridge 370.

Typically, an Excimer laser is used to form the interrogation apertures 408 and alignment apertures 430 and 432. A DPSS laser is generally used to form all of the other channel and aperture structure (filters, vents, channels, etc.). An excimer laser can cut the currently preferred 44 μm diameter interrogation aperture 408 within ±2 microns. Repeatability of the DPSS laser is more like plus/minus 5 microns. The large alignment holes 430, 432 are manufactured (laser cut)

with extreme precision relative to the laser drilled interrogation aperture 108. Use of the more accurate laser allows the interrogation aperture 408 to be mechanically aligned, from cassette to cassette, to the excitation radiation beam of a preferred interrogation device with an accuracy of about 20 µm to 50 µm. Here, "accuracy" means that the center of the aperture is disposed within a repeatable "accuracy" radius of the theoretical centerline of an interrogation location provided by a cooperatingly structured interrogation device.

Figure 11:
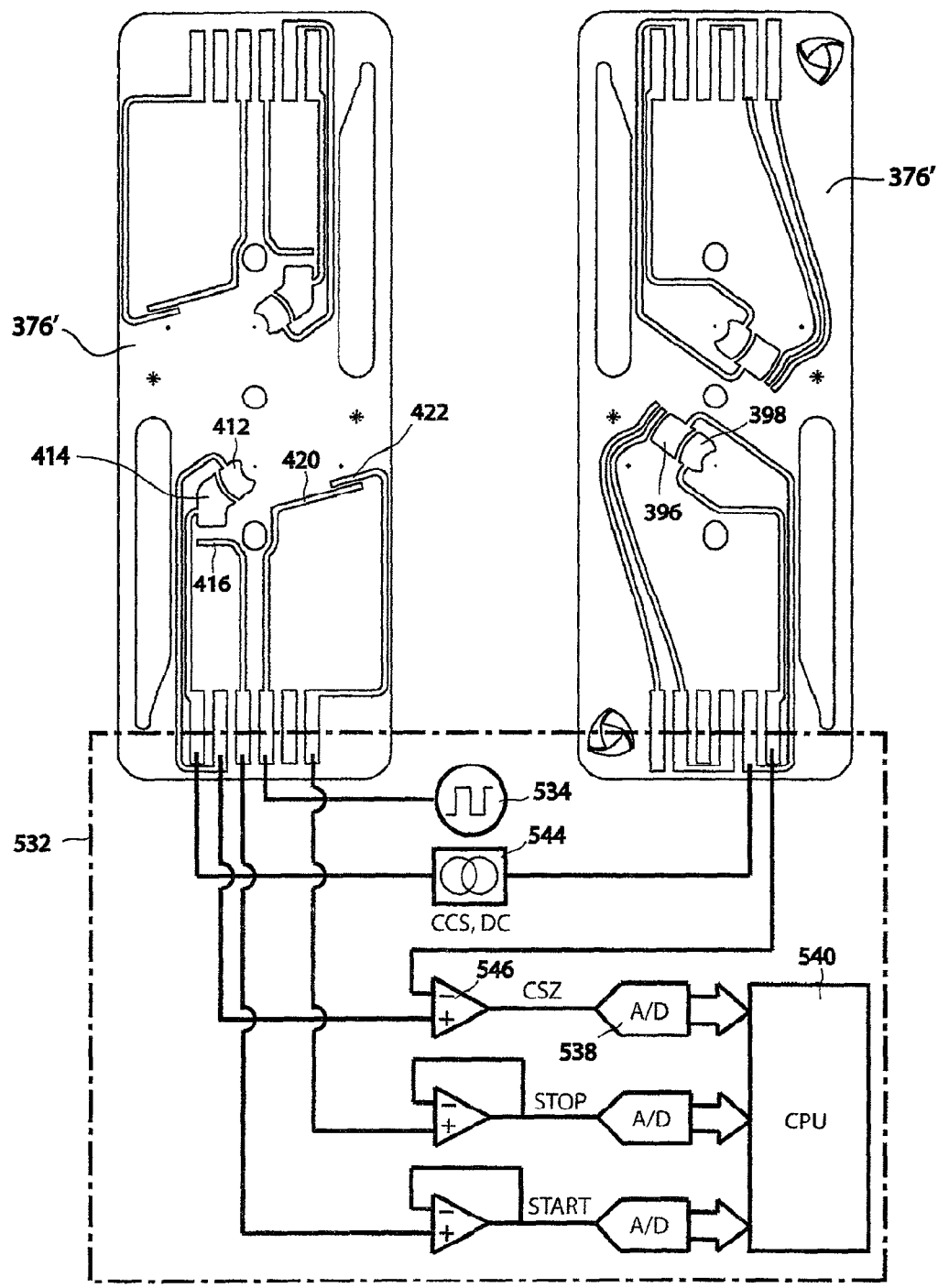
FIG. 11 is a butterfly plan view schematic of an interrogation portion, of a cassette similar to that illustrated in FIGS. 6-10, interfacing with a schematic representative of an interrogation apparatus.

FIG. 11 illustrates an interrogation layer of a cassette structured for electrical fluid position detection and optically-based particle interrogation interfacing with electrically-based interrogation structure of an interrogation apparatus, such as apparatus 100. Electrical interrogation structure 532 illustrated in FIG. 11 is only a partial schematic to illustrate selected operation desired between an exemplary cassette and an interrogation apparatus 100. Note: only the interrogation layer 376' of a single cassette, similar to cassette 370, is illustrated, but is butterflied to show both sides simultaneously. Electrical interrogation structure, such as indicated by dashed box 532, is desirably included in structure provided by an apparatus 100. A conventional electrical edge connector can conveniently couple a cassette to communicate with interrogation electronics the apparatus 100. One or more electrical signal may be applied to one or more contact pad to provide a stimulus signal to sample fluid in the cassette. A workable signal includes a 50 kHz, square-wave, 30 mV p-p oscillating electrical signal, e.g. such as might be applied by signal generator 534.

An electrical signal may be monitored with respect to ground at an electrode to determine fluid behavior inside the cassette. When the circuit monitored is no longer open, the fluid boundary has at least reached the monitored electrode. An uninterrupted match to the applied signal as fluid continues to flow will indicate lack of bubbles in the sample fluid. The leading edge of the fluid boundary will be determined by successive closed circuits formed by the electrolytic fluid contacting downstream electrodes. Signals may be converted by an A/D converter 538, and passed to the computer processing unit 540. Optically-based data may be obtained (using structure such as illustrated in FIGS. 1-4 and previously described) at selected instances in time that may be triggered, for example, by one or more monitored signal, or periodically, or continuously.

In detail, a start trigger signal potential may be created by application of a time-varying signal from signal generator 544 to the contact pad that communicates to electrode 414. A signal is monitored at the contact pad that communicates with trigger electrode 416. When a signal (e.g. not open-circuit) is first detected at electrode 416, the fluid sample has wet-out the driven electrode 414, and the fluid front boundary is at the location of electrode 416, so collection of test data may be started responsive to that detection of that signal. The central processing unit 540 can be variously programmed to cause multiple responses to different inputs, such as to: start and/or stop a test, cause data collection, apply a reduced pressure profile to a cassette, maintain a desired vacuum, plot data, and even discriminate between installed cassettes to run a test corresponding to the particular cassette type, and the like.

A stop trigger signal potential may be created by application of a signal from signal generator 534 to the contact pad that communicates to electrode 420. A signal is monitored at the contact pad that communicates with trigger electrode 422. When a signal (e.g. not open-circuit) is first detected at electrode 422, the fluid sample has wet-out the driven electrode 420, and the fluid front boundary is at the location of electrode 422. The signal is passed to CPU 540, and the data collection and reduced pressure can be stopped in accordance with programmed behavior of interrogation apparatus 100. Generally, it is desirable to terminate at least the applied vacuum before the sample fluid is drawn significantly beyond the stop trigger and escapes from the cassette 370.

To detect particles in an interrogation zone according to a preferred variation of the Coulter effect in the structure illustrated in FIG. 12, a Direct Current, constant current source signal is applied by signal generator 544 between a contact pad communicating with driving electrode 414 and the contact pad communicating with driving electrode 396. A workable arrangement includes applying +15 Volt at one contact pad, and −15 Volts at the other contact pad. Voltage change responsive to particle travel through an orifice is monitored between detection electrodes 412 and 398. The monitored differential signal is transmitted by an operational amplifier 546 and converted to digital format by an A/D converter 538, then passed to the CPU 540 for further processing.

During use of an interrogation apparatus, such as apparatus 100, a removable microfluidic cassette 104 is installed in an initial position that is controlled by indexing structure of apparatus 100. Collimated Laser light (e.g. 488 nm light) will exit the laser and pass thru a short pass optical filter (that will remove any unwanted longer wavelengths, e.g. >490 nm). This collimated light will pass through a lens to focus it down to a diameter (e.g. about 40 µm) just smaller than the cell detection aperture in the interrogation layer. An optional restricting orifice can remove any unwanted fringe light prior to passing through a focusing lens. Once through the focusing lens, the light may reflect off a mirror connected to a piezo steering table (or equivalent). Such a mirror will be actively steered, using on-board CPU feedback from either an optical diode underneath the sensor or from the primary photodetectors (PMTs or APD) to either maximize or minimize the signal (maximize if using the diode under the sensor, min. if using the PMTs). Making a relative adjustment between a stimulation radiation beam and detection/interrogation aperture will typically be done each time a new cassette is inserted into the system, and may even be performed during a test. The primary laser light will desirably pass perfectly through the detection aperture 106. It will then typically flow into a light trap to prevent any of this light from feeding back into the system.

A fluid sample may be prepared and loaded into the cassette in conventional fashion. A representative diluted blood sample size is about 75 µl, which is processed in about 15 seconds. During a test on one type of fluid sample, cells carried in a diluent fluid will then begin to flow through the detection aperture 106. As they do, fluorescently labeled cells (or any particle such as beads) will emit secondary light at a higher wavelength (Stokes-shifted). This longer wavelength emission light will be emitted from the cell/particle in every direction, including up. Because it is at a longer wavelength, the emitted light will pass directly through the dichroic mirror toward the primary optical detectors (PMTs or APDs). Multiple photodetectors can be used. It is currently preferred to provide systems with 2 to 4 detectors. Dichroic mirrors are again used to reflect shorter wavelength light to the closer detectors with increasing wavelength being reflected as each subsequent detector. For example, the dichroic mirrors may have cutoffs of 550 nm, 650 nm, and 730 nm in a four photodetector system. As appreciated by one skilled-in-the-art, an indicated "numerical value" for "wavelength" actually encompasses a band about that numerical value.

This latter system would allow for simultaneous four color detection and Coulter impedance particle sizing. It would also be able to do volumetric counts using appropriately structured cassettes. Advantages include small and convenient system size, low test cost, portability, and the cassette offers zero maintenance. The system may be embodied to provide what is believed to be the worlds first tablet flow cytometer.

In use of a preferred embodiment, a cell sample may be prepared using one or more fluorescent labels. Of note, this system can be used to analyze multiplex bead-based assays. The sample is typically inserted into a microfluidic cassette using a pipette or similar tool. The cassette is inserted into the system and the door is closed. The laser is turned on and automatically aligned (e.g. via beam steering and feedback from either the underside photodiode or one of the measurement PMTs, or both). Once aligned, the vacuum system applies a constant suction to the cassette to start the sample moving through fluid channels in the cassette. The fluid first flows through the debris filter which acts to break cells up (disassociate them) and prevent large particles from clogging the detection zone. The fluid then flows over the first two electrodes (one stimulus and one measurement), flows through the interrogation aperture and over the next two electrodes (second stimulus and second measurement). The fluid then hits the start electrode and the test officially "starts". Coulter measurements are made simultaneously to the emission fluorescence measurements until the final stop electrode is contacted by the sample fluid and generates a "stop" signal. Data will generally be displayed in either multiple histogram formats or scatter (dot) plots.

While the invention has been described in particular with reference to certain illustrated embodiments, such is not intended to limit the scope of the invention. The present invention may be embodied in other specific forms without departing from its spirit or essential characteristics. The described embodiments are to be considered only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A microfluidic interrogation apparatus, comprising:
    indexing structure effective to hold a microfluidic device at an installed position such that an interrogation aperture of said microfluidic device is urged near to a desired location, said microfluidic device being of the type comprising a first channel segment disposed on one side of an opaque layer, said interrogation aperture being structured and arranged to communicate fluid from said first channel segment to a second channel segment disposed on the opposite side of said opaque layer, and fluid flow in said first channel segment and said second channel segment being generally parallel to said opaque layer, said microfluidic device being structured and arranged to urge particles of interest through said interrogation aperture in a substantially single-file arrangement;
    a source of stimulation radiation structured to emit radiation as a beam oriented for propagation of radiation in a particular direction;
    adjustment means to refine alignment of said interrogation aperture, from an initially installed position, and with respect to said beam, to maximize beam propagation through said aperture in a direction congruous with a centerline of said interrogation aperture;
    sensor means disposed to provide steering feedback to said adjustment means; and
    a first photodetector disposed to detect Stokes-shift emission radiation from a particle disposed inside said interrogation aperture.

2. The apparatus according to claim 1, wherein:
    said adjustment means comprises steering means configured to change the disposition of a path of propagation of said beam.

3. The apparatus according to claim 2, wherein:
    said steering means comprises a mirror affixed to a steering table.

4. The apparatus according to claim 1, wherein:
    said adjustment means comprises X-Y displacement means structured to move said beam into alignment with said microfluidic device.

5. The apparatus according to claim 1, wherein:
    said adjustment means comprises X-Y displacement means structured to move said microfluidic device into alignment with said beam.

6. The apparatus according to claim 1, wherein:
    said sensor means comprises an optical diode disposed on an exit side of said interrogation aperture with respect to said stimulation radiation.

7. The apparatus according to claim 1, wherein:
    said sensor means comprises a photodetector disposed on an entrance side of said interrogation aperture with respect to said stimulation radiation.

8. The apparatus according to claim 1, wherein:
    said adjustment means is automated.

9. The apparatus according to claim 1, wherein:
    said adjustment means comprises manual manipulation by a user of said apparatus.

10. The apparatus according to claim 1, wherein:
    said source of stimulation radiation comprises a laser directed through a focusing lens to form a coherent beam, said coherent beam having a characteristic cross-section size that is smaller than a characteristic size of a cooperating cross-section of said interrogation aperture.

11. The apparatus according to claim 10, further comprising:
    a restricting orifice disposed in a path of said beam and upstream of said aperture, said orifice being structured to resist passage of fringe radiation to improve coherence of said beam downstream of said orifice.

12. The apparatus according to claim 1, wherein:
    said indexing structure comprises a first pin structured for reception in a first socket of said microfluidic device, said first pin and said first socket cooperating to cause said first socket of an installed microfluidic device to be positioned at a known X-Y coordinate with respect to said apparatus.

13. The apparatus according to claim 12, further comprising:
    a second pin structured for reception in a second socket of said microfluidic device, said second pin and said second socket cooperating to cause said installed microfluidic device to be positioned at a known angular orientation with respect to said first pin.

14. The apparatus according to claim 1, wherein:
    said source of stimulation radiation comprises a laser directed through a focusing lens to form a coherent beam;
    a steerable first minor is disposed downstream of said lens to redirect said beam for reflection from a second minor and into an interrogation aperture of an installed microfluidic device, said second minor being a dichroic mirror; and
    said apparatus is structured and arranged such that Stokes-shift emission radiation from a particle disposed in said interrogation aperture may propagate along an emission radiation path through said second mirror for detection by a first photodetector.

15. The apparatus according to claim 14, further comprising:
a plurality of photodetectors, each such photodetector being associated with a minor disposed in said emission radiation path and adapted to direct emission radiation from said emission radiation path toward a photodetector.

16. The apparatus according to claim 15, further comprising:
a minor element disposed upstream of said photodetectors and arranged to change a direction of propagation of said emission radiation path to permit compact assembly of said apparatus.

17. The apparatus according to claim 1, wherein:
said source of stimulation radiation comprises a laser directed through a focusing lens to form a coherent beam, said beam being directed for propagation through a first dichroic minor and into said interrogation aperture, said first dichroic mirror being structured and arranged such that Stokes-shift emission radiation from a particle disposed in said interrogation aperture may propagate along an emission radiation path for reflection from said first dichroic mirror and subsequent detection by a first photodetector.

18. The apparatus according to claim 17, further comprising:
a plurality of photodetectors, each such photodetector being associated with a mirror disposed in said emission radiation path downstream from said first dichroic mirror and adapted to direct emission radiation from said emission radiation path toward a photodetector.

19. The apparatus according to claim 1, wherein:
said apparatus is structured to fit inside an envelope having a volumetric size of less than about 6 inches by about 9 inches by about 3 inches.

20. A method of using the apparatus according to claim 1, comprising:
installing a microfluidic device into initial registration with respect to said apparatus;
adjusting a relative position of said device with respect to said beam to minimize autofluorescence caused by impingement of said beam onto a portion of said device;
processing a sample of particle-carrying fluid to detect Stokes-shift radiation from one or more particle of interest in said sample; and
removing said microfluidic device from said apparatus.

21. The method according to claim 20, wherein:
said apparatus further comprises electrical circuitry adapted to cooperate with said microfluidic device to permit detection of Coulter effect phenomena due to travel of one or more particle of interest through said interrogation aperture;
the method further comprising:
using said apparatus simultaneously to detect Coulter effect phenomena and Stokes-shift emission while processing said sample.

* * * * *